United States Patent [19]

Pilliar

[11] 4,206,516
[45] Jun. 10, 1980

[54] SURGICAL PROSTHETIC DEVICE OR IMPLANT HAVING PURE METAL POROUS COATING

[75] Inventor: Robert M. Pilliar, Toronto, Canada

[73] Assignee: Ontario Research Foundation, Sheridan Park, Canada

[21] Appl. No.: 858,417

[22] Filed: Dec. 7, 1977

[30] Foreign Application Priority Data

Dec. 15, 1976 [GB] United Kingdom ............... 52410/76

[51] Int. Cl.$^2$ ........................... A61F 1/24; A61F 1/00
[52] U.S. Cl. ............................................... 3/1.9; 3/1; 128/92 C
[58] Field of Search ................................. 3/1.9–1.913, 3/1; 128/92 C

[56] References Cited

U.S. PATENT DOCUMENTS

| | | | |
|---|---|---|---|
| 3,852,045 | 12/1974 | Wheeler et al. | 3/1.9 X |
| 3,855,638 | 12/1974 | Pilliar | 3/1 |
| 4,017,911 | 4/1977 | Katesjian et al. | 3/1.5 |
| 4,101,984 | 7/1978 | MacGregor | 3/1 X |

*Primary Examiner*—Ronald L. Frinks
*Attorney, Agent, or Firm*—Sim & McBurney

[57] ABSTRACT

A surgical prosthetic device or implant is disclosed consisting of a coherent metal substrate and a pure metal porous coating. The pure metal porous coating is formed by thermal decomposition of a coating of thermally-decomposable metal compound particles and sintering of the metal particles so formed. The surface of the device or implant is irregular but the porosity is substantially uniformly distributed throughout the coating. The coating is strongly adherent to the substrate and supports the ingrowth of bone tissue for fixation of the device or implant in the body. Such coating also supports the ingrowth of fibrous tissue for the attachment of tendons and ligaments to the device.

7 Claims, No Drawings

SURGICAL PROSTHETIC DEVICE OR IMPLANT HAVING PURE METAL POROUS COATING

FIELD OF INVENTION

This invention relates to surgical prosthetic devices having porous metal coatings on substrate surfaces.

BACKGROUND OF THE INVENTION

In U.S. Pat. No. 3,855,638 to Ontario Research Foundation, there are described surgical prosthetic devices and implants consisting of a metal substrate with a porous metal coating into which bone tissue may grow for incorporation of the prosthesis into the body. The porous metal coating comprises metal particles joined to each other and to the substrate to define a plurality of connected, interstitial pores uniformly distributed throughout the coating. The resulting porous coating is composed of regularly-shaped particles. The average interstitial pore size is at least about 50 microns to ensure bone tissue ingrowth for incorporation of the device into the body. The term "metal" as used therein (and also herein) refers to both pure metal and metal alloys.

As described in the earlier U.S. Patent, such composite articles may be formed by sintering procedures using metal particles of the required particle size, preferably about −100+325 mesh (about 50 to about 200 microns), the term "mesh" referring to the U.S. Standard Sieve mesh series.

Certain pure metals which otherwise are suitable for the formation of coatings on surgical prosthetic devices and implants are pyrophoric at very fine particle sizes. One such pure metal is titanium which is an attractive material of construction for a porous coating of a surgical prosthetic device or implant owing to its strength, inert character and light weight.

SUMMARY OF INVENTION

In accordance with the present invention, there is provided a surgical prosthetic device or implant comprising a coherent metal substrate and an adherent porous lpure metal coating having a network of interconnected pores substantially uniformly distributed therethrough and formed by the decomposition of a coating of particles of a metal compound, or a mixture of metal compounds, which is decomposable to the pure metal, in engagement with the coherent metal substrate.

GENERAL DESCRIPTION OF INVENTION

The porosity of the coating is usually in the range of about 10 to about 40% and the coating usually has a thickness of about 100 to about 1000 microns. Thick layers may, however, be formed by multiple layering of the metal compound particles.

The particle size of the metal compound particles is chosen to ensure that the resulting interstitial pore size is at least sufficient to permit bone tissue to grow into the porous coating for incorporation of the prosthetic device or implant into the body. The interstitial pore size suitable for ingrowth of bone tissue also is suitable for the ingrowth of fibrous tissue, such as, soft body tissues, and tendon or ligament tissue. The device or implant, therefore, may be used for ligament and tendon fixation, if desired.

Usually, the particle size should be +325 mesh (greater than about 50 microns). Preferably, the particle size is also −100 mesh (less than about 200 microns).

Soft tissues generally can grow into smaller openings than bone tissue and, hence, in instances where both bone tissue ingrowth and soft tissue ingrowth are required, the portions of the device or implant required to receive soft tissue ingrowth may be coated with a porous coating formed from finer particle size particles than those used for the coating required to receive bone tissue ingrowth.

Microscopic examination of the porous surface provided in this invention reveals an irregular surface having irregularly-shaped particles, in contrast to the surface provided in U.S. Pat. No. 3,855,638. The irregularly-shaped particle surface provided in this invention behaves in very similar fashion to that provided in U.S. Pat. No. 3,855,638, with respect to coating-substrate interface strength and bone tissue ingrowth, with consequent fixation and incorporation into the body.

While usually a pure metal porous coating is provided on a coherent substrate of the same pure metal in this invention, the invention also encompasses the provision of a pure metal porous coating on a coherent substrate of a different pure metal or of a metal alloy.

The coating is usually provided only on those portions of the prosthetic device or implant which it is desired to be fixed to bone and other tissue. In certain applications, only a portion of the device or implant is required to have the porous coating while in others, the whole of the device or implant is coated. Additionally, as previously mentioned, portions of the device may have a porous coating of one pore size while other portions of the device may have a porous coating of another pore size.

In a particularly preferred embodiment of the invention, a porous coating of titanium having a network of interconnected pores substantially uniformly distributed therethroughout of porosity of about 10 to about 40% is provided on a coherent titanium metal substrate by thermal decomposition of titanium hydride particles on the metal substrate. The titanim hydride particles have a particle size of +325 mesh, preferably −100+325 mesh.

A variety of techniques may be used to form the product of the present invention. The procedures will be described with reference to the formation of the preferred embodiment of the invention using titanium hydride particles but it will be obvious to those skilled in the art that equivalent procedures may be used with particles of other thermally decomposable compounds.

Generally, the outer surface of the titanium metal substrate having the desired shape of the prosthetic device or implant first is roughened to enhance adherence of the porous coating to the surface, for example, by blasting with an abrasive material.

Thereafter, a coating of the titanum hydride particles of the desired thickness is formed on the roughened surface. The coating may be formed by spraying the roughened surface with a binder and then suspending the article in a fluidized bed of titanium hydride particles of the desired particle size distribution to form the coating by adherence of the particles to the binder. The article is withdrawn from the fluidized bed and the binder allowed to dry.

In an alternative procedure, the titanium hydride particles may be mixed with a binder to form a fairly viscous slurry which then is spray applied to the roughened surface to form the coating thereon, and the coating then is allowed to dry.

Another coating procedure involves the formation of a slurry of the titanium hydride particles in a binder and the dipping of the article in the slurry. After allowing excess material to run off, the coated body may be dried.

After the formation of the dried coating on the substrate, the preform is heated to an elevated temperature to cause thermal decomposition of the titanium hydride and the formation of a porous coating of titanium metal particles which are connected together at their points of contact with each other and the substrate to define a network of interconnected pores substantially uniformly distributed throughout the coating. Generally, the heating is conducted under a vacuum to remove the hydrogen formed in the decomposition.

The heating usually is conducted in two stages, namely, thermal decomposition and sintering. The preform is heated to the sintering temperature over a period of time to permit all the titanium hydride particles to be thermally decomposed prior to sintering.

Hydrogen evolution usually commences about 500° C. and sintering is usually effected about 1200° to about 1300° C. Once the sintering temperature is attained, the preform is maintained at that temperature to complete the sintering operation.

Following formation of the porous coating, it may be machined and refined, if desired, to improve its surface characteristics.

The product which is formed by the above-described procedure has a high particle-particle and coating-substrate shear strength, generally in excess of about 2000 psi, so that the product is suitable for bone tissue ingrowth applications.

EXAMPLE

Titanium metal plugs of 60 mm length and 6 mm diameter were roughened, a binder spray applied to the surface and titanium hydride particles of size $-100+325$ mesh were applied to the surface from a fluidized bed to a coating thickness of about 100 microns.

The coated plugs were placed in an enclosed chamber to which a vacuum of $10^{-5}$ to $10^{-6}$ mm Hg was applied to remove hydrogen as it is formed. The plugs were heated up to about 1250° C. in about 3 hours, and held at that temperature for a further three hours.

An irregular coating surface resulted which had a uniformity of pore distribution throughout the coating. The porosity was estimated to be about 30%. The properties of these samples were tested against the properties of similar coated plugs formed by the procedure of U.S. Pat. No. 3,855,638 having a regular surface.

A hole was formed through the cortex of the tibia of several dogs and plugs snug fit in position in the holes. Some of the dogs were sacrificed after 1 month while others were sacrificed after 3 months. Force was applied to the plugs to attempt to push the plugs out of the holes. In some cases, the bone fractured rather than a pushout being achieved. In others, a stress of about 2,000 psi was necessary to push out the samples indicating bone tissue ingrowth into the surface. In these cases, the ingrown bone tissue had fractured thereby permitting plug push-out.

The present invention, therefore, provides a surgical prosthetic device or implant comprising a composite of a metal substrate and a porous pure metal coating having a uniform distribution of interconnected pores therethrough. Modifications are possible within the scope of this invention.

What I claim is:

1. A surgical prosthetic device or implant comprising a composite structure consisting of a coherent solid metal substrate and a porous coating of at least one pure metal adhered to and extending over at least part of the surface of said substrate to a thickness of at least about 100 microns and having a porosity of about 10 to about 40%, said metal and pure metal being substantially non-corrodable and non-degradable by body fluids, said porous coating having an irregular surface and a plurality of connected interstitial pores substantially uniformly distributed therethrough, said porous coating being formed by thermal decomposition of particles of at least one thermally-decomposable compound of said at least one pure metal and sintering of the thermally decomposed particles to cause bonding of the resulting irregularly-shaped pure metal particles to each other and to said substrate at their points of contact therewith, said particles of pure metal compound having a size at least sufficient to provide interstitial pores in said coating and the surface thereof which will permit the growth of bone tissue into said coating.

2. The device of claim 1 wherein said metal compound particles have a diameter of +325 mesh.

3. The device of claim 2 wherein said metal compound particles have a diameter of +325−100 mesh.

4. The device of claim 1 wherein said metal compound is titanium hydride.

5. The device of claim 4 wherein said substrate is made of a titanium alloy.

6. A surgical prosthetic device or implant comprising a composite structure consisting of a coherent solid titanium substrate and a porous coating of titanium adhered to and extending over at least part of the surface of said substrate to a thickness of at least about 100 microns and having a porosity of about 10 to about 40%, said porous coating having an irregular surface and a plurality of connected interstitial pores substantially uniformly distributed therethrough and being formed in a single heating step by thermal decomposition of titanium hydride particles having a particle size distribution +325−100 mesh and sintering of the thermally decomposed particles to cause bonding of the resulting irregularly-shaped titanium particles to each other and to the substrate at their respective point of contact.

7. The device of claim 6 wherein said porous coating has a thickness from about 100 to about 1000 microns.

* * * * *